United States Patent [19]

Nishimura et al.

[11] 4,351,967
[45] Sep. 28, 1982

[54] PROCESS FOR PRODUCING PHENOLIC COMPOUNDS

[75] Inventors: Tadahiko Nishimura, Iwakuni; Hiroshi Yamamoto, Ichihara; Masatoshi Osuo, Ichihara; Akio Kanazawa, Ichihara, all of Japan

[73] Assignee: Mitsui Petrochemical Industries, Ltd., Tokyo, Japan

[21] Appl. No.: 202,482

[22] Filed: Oct. 31, 1980

[30] Foreign Application Priority Data

Nov. 2, 1979 [JP] Japan .................. 54-142448

[51] Int. Cl.³ .............................. B01D 3/40
[52] U.S. Cl. ...................... 568/754; 203/64; 568/798
[58] Field of Search ............ 568/749, 754, 798; 203/63, 64, 71, 76, 75, 78, 79, 82, 83, 84, 85, 95-97

[56] References Cited

U.S. PATENT DOCUMENTS 2,597,497  5/1952  Joris ........................... 568/754
3,184,398  5/1965  Schumacher et al. ........ 203/96
3,215,745  11/1965  Frank ......................... 568/754

Primary Examiner—Frank Sever
Attorney, Agent, or Firm—Sherman & Shalloway

[57] ABSTRACT

In an improved process for recovering a phenolic compound, the improvement comprising, subjecting a phenolic containing fraction recovered overhead in an extractive distillation, to a subsequent steam distillation; recovering the phenolic product as a bottoms fraction therefrom, and recycling such product to some point upstream in the process.

11 Claims, 1 Drawing Figure

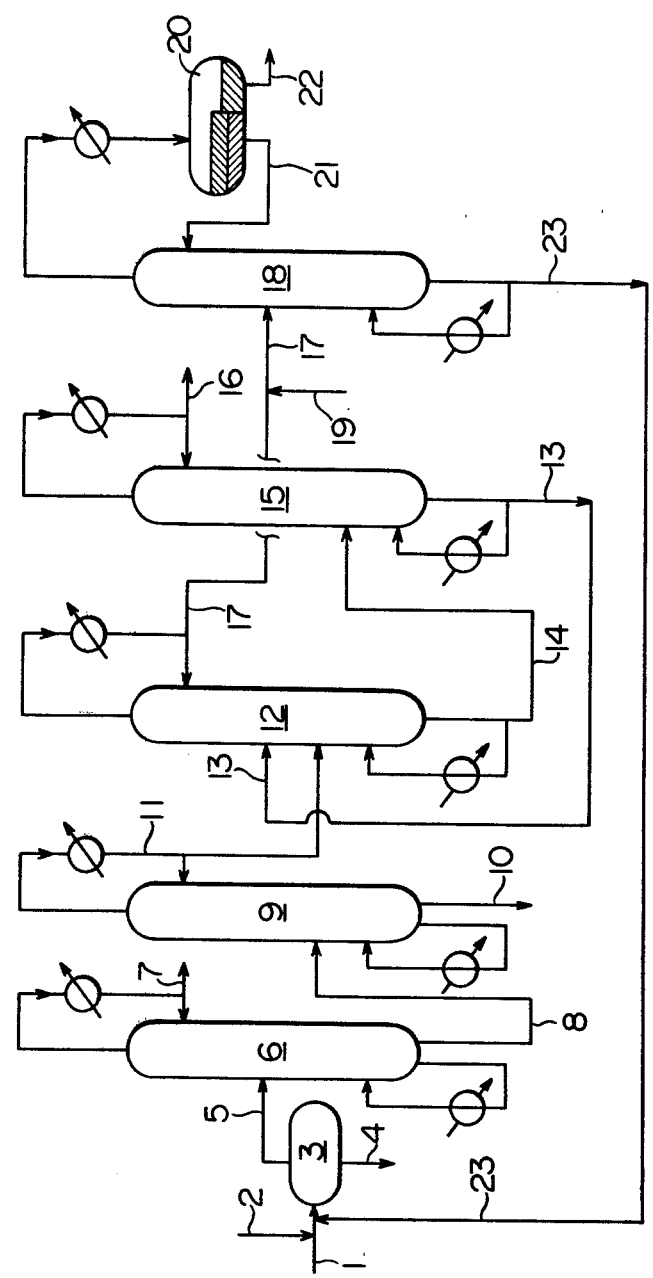

PROCESS FOR PRODUCING PHENOLIC COMPOUNDS

This invention relates to an improvement in and relating to a process for producing phenolic compounds. More specifically, this invention relates to an industrially advantageous process for producing phenolic compounds in pure form by the catalytic acid cleavage of aralkyl hydroperoxides such as cumene hydroperoxide.

Industrially, phenolic compounds are produced by the catalytic acid cleavage of aralkyl hydroperoxides represented by the following formula

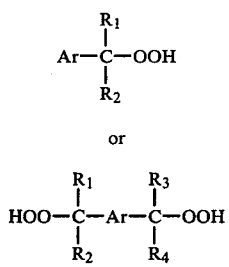

wherein Ar represents a phenyl ring, and $R_1$, $R_2$, $R_3$ and $R_4$, independently from each other, represent a lower alkyl group. For example, phenol is produced by contacting cumene hydroperoxide obtained by air oxidation of cumene with an acid such as sulfuric acid to decompose the cumene hydroperoxide into phenol and acetone, and separating the phenol from the acid cleavage product.

The catalytic acid cleavage product of cumene hydroperoxide contains many impurities, for example salts of the acid used in the acid cleavage; ethylbenzene and m- and/or p-diisopropylbenzene carried over by the starting cumene; the unreacted cumene; acetophenone, phenyldimethyl carbinol, mesityl oxide and hydroxyacetone which occur as by-products in the air oxidation of cumene and the catalytic acid cleavage of cumene hydroperoxide; and 2-methylbenzofuran, 2,3-dimethylbenzofuran and other high-boiling by-products which are secondary reaction products of the aforesaid impurity compounds; in addition to phenol and acetone which are main reaction products. These impurities cannot be removed fully by an ordinary fractional distillation procedure.

In an attempt to purify the crude phenol produced by such a method, Japanese Patent Publication No. 5713/61 proposes a method for producing purified phenol which comprises catalytically cleaving cumene hydroperoxide with an acid, neutralizing the acid in the resulting acid cleavage product, removing the unreacted material, acetone and lower-boiling fractions, the reaction solvent, water, etc. by fractional distillation, optionally distilling the residue to remove by-products having a higher boiling point than phenol, and extractively distilling the resulting crude phenol in the presence of a polyalkylene glycol or its ether having a higher boiling point than the crude phenol.

Purification of crude phenol by extractive distillation as disclosed in the above-cited Japanese Patent Publication No. 5713/61 is one of commercially feasible purifying methods, but is not entirely satisfactory leaving a problem still to be solved. For example, phenol obtained by this method contains impurities which cause undesirable coloration when it is treated with chlorine or sulfonated with sulfuric acid in order to convert it to a useful industrial material. Accordingly, the phenol produced by this method has only limited utility in converting it to phenol derivatives having a higher industrial value, especially where phenol of high quality is required as a starting material. Moreover, depending upon the types of the impurities, the aforesaid phenol may degrade the quality of the polyalkylene glycol or its ether used in extractive distillation, in which case the extractive distillation solvent has to be regenerated.

One method for solving this problem was proposed by the present inventors in Japanese Patent Publication No. 1258/75. This method comprises removing acetone and lower boiling impurities from the acid cleavage product by distillation prior to extractive distillation of the crude phenol with a polyalkylene glycol or its ether, adjusting the remaining fraction to an unreacted cumene content of 0.2 to 1.2 parts by weight per part by weight of phenol and a water content to 0.2 to 1.2 parts by weight per part by weight of phenol, then distilling the fraction under reduced pressure, removing fractions containing water and cumene from the top of the distillation column, introducing crude phenol obtained from the bottom of the column, from which the aforesaid impurities have been partly removed in advance, to an extractive distillation column, fractionally distilling it in the presence of a polyalkylene glycol or its ether to remove impurities contained in the crude phenol, and separating high purity phenol from a mixture consisting of phenol and the polyalkylene glycol or its ether.

It has been ascertained that this improved method is effective in actual industrial operations. Since, however, acetone and lower boiling fractions must be removed in advance and the method is effective when cumene is present in a sufficient amount in the acid cleavage product, this method is not applicable equally to all processes used in the production of phenols by the cumene method.

It is an object of this invention to provide a process which can be industrially applied to the production of high-purity phenolic compounds in high yields, and which is free from the defects of the previously suggested methods.

Other objects and advantages of this invention will become apparent from the following description.

According to this invention, there is provided in a process for producing a phenolic compound which comprises a step of catalytically cleaving an aralkyl hydroperoxide with an acid to form a phenolic compound, a step of removing the acid and by-products or impurities having lower and/or higher boiling points than the resulting phenolic compound to recover a crude phenolic compound, a step of feeding the recovered crude phenolic compound to an extractive distillation column and extractively distilling it in the presence of a polyalkylene glycol or its ether having a higher boiling point than the phenolic compound to separate the phenolic compound and the polyalkylene glycol or its ether as a bottom fraction, and a step of separating the bottom fraction into the phenolic compound and the polyalkylene glycol or its ether; the improvement wherein (a) the extractive distillation is carried out under such conditions that the phenolic compound comes out from the top of the column in an amount of 0.3 to 30% by weight based on the total weight of the phenolic compound in the crude phenolic compound fed to the extractive distillation column, and (b) the phenol compound-containing overhead fraction from the extractive distillation column is subjected to steam distillation and the resulting bottom fraction containing the phenolic compound is recycled to any step after said step of catalytic acid cleaving and before said step of extractive distillation.

In the first step of the process of this invention, the aralkyl hydroperoxide is subjected to acid catalytic acid cleavage. Generally, the aralkyl hydroperoxide is produced by air oxidizing in an ordinary manner an alkylbenzene such as cumene, m-cymene, p-cymene, m-diisopropylbenzene and p-diisopropylbenzene, and encompasses the compounds represented by formula (I) or (II) given hereinabove. Specific examples of the aralkyl hydroperoxide are cumene hydroperoxide, m-cymene hydroperoxide, p-cymene hydroperoxide, p-diisopropylbenzene hydroperoxide, and m-diisopropylbenzene hydroperoxide. In the process of this invention, cumene hydroperoxide m-cymene hydroperoxide and p-cymene hydroperoxide, are preferably used. Cumene hydroperoxide is especially preferred.

The aralkyl hydroperoxide is cleaved into a phenolic compound and a ketone by contacting it with an acid such as sulfuric acid, hydrochloric acid, a silica-alumina type solid acid, or a strong acid-type ion exchange resin in accordance with methods known as a cleavage reaction. For example, phenol and acetone are prepared from cumene hydroperoxide; m-cresol and acetone, from m-cymene hydroperoxide; p-cresol and acetone, from p-cymene hydroperoxide; hydroquinone and acetone, from p-isopropylbenzene hydroperoxide; and resorcinol and acetone, from m-diisopropylbenzene hydroperoxide.

The catalytic acid cleavage product contains various by-products or impurities depending upon the type of the aralkyl hydroperoxide or the acid used, the contacting conditions, etc. in addition to the desired phenolic compound. For example, the product of cleavage of cumene hydroperoxide with sulfuric acid contains sulfuric acid, a solvent used in the catalytic acid cleavage step (e.g., cumene), mesityl oxide, hydroxyacetone, 2-methylbenzofuran, 2,3-dimethylbenzofuran, acetaldehyde, propionaldehyde isobutyraldehyde, alpha-methylstyrene, acetophenone, phenyldimethyl carbinol and other high boiling compounds of unknown structures as main by-products or impurities in addition to the main products, phenol and acetone.

Prior to extractive distillation, the catalytic acid cleavage product is subjected to a step of removing the acid and by-products having lower and/or higher boiling points than the phenolic compound to recover a crude phenolic compound.

This step of recovering the crude phenolic compound can be performed by any conventional methods. A typical method comprises neutralizing the catalytic acid cleavage product with sodium hydroxide and/or sodium phenolate, removing the salt formed by neutralization, removing a ketone such as acetone by distillation, further distilling the resulting distillation bottoms to remove most of components having lower boiling points than the phenolic compound (e.g., water, cumene and alpha-methylstyrene) to distill out a crude phenolic compound and remove high boiling compounds as distillation bottoms. If desired, the crude phenolic compound may be recovered in the above method by removing components having lower boiling points than the phenolic compound including a ketone such as acetone in one distilling operation.

The crude phenolic compound so recovered generally contains at least about 95% by weight, usually 97 to 99.5% by weight, of a phenolic compound although its content may vary depending upon the procedure used in the recovering step, and contains impurities in the following approximate proportions.

| | |
|---|---|
| Low-boiling hydrocarbon compounds including cumene and α-methylstyrene: | about 70 to 90 wt. % |
| High-boiling compounds including 2-methylbenzofuran and 2,3-dimethylbenzofuran: | about 5 to 20 wt. % |
| Ketones including acetophenone, mesityl oxide and hydroxyacetone: | about 5 to 15 wt. % |

The crude phenolic compound of this composition is then fed into an extractive distillation column where it is extractively distilled in the presence of a polyalkylene glycol or its ether.

The polyalkylene glycol or its ether used in the extractive distillation has a higher boiling point than the phenolic compound in the crude phenolic compound, preferably has a boiling point at least 20° C. higher than the phenolic compound. Suitable polyalkylene glycols or the ethers thereof are expressed generally by the following formula

$$R_5-O-R_6-O)_nR_7 \qquad (I)$$

wherein $R_5$ or $R_7$ are identical or different and each represent a hydrogen atom or a lower alkyl group, $R_6$ represents a lower alkylene group, and n is an integer of 1 to 4, especially 1 to 3.

The term "lower," as used in the present application to qualify a group or a compound, means that the group or the compound so qualified has not more than 6, preferably not more than 4, carbon atoms.

In the above formula, examples of the lower alkyl group are methyl, ethyl, n- or iso-propyl, and n-, iso-, sec- or tert-butyl. The lower alkylene group includes ethylene, propylene, 1,2-propylene, and 2,2-dimethylpropylene.

Specific examples of suitable polyalkylene glycols or the ethers thereof include polyalkylene glycols such as diethylene glycol, triethylene glycol and dipropylene glycol, and polyalkylene glycol ethers such as diethylene glycol methyl ether, diethylene glycol ethyl ether, diethylene glycol propyl ether and diethylene glycol butyl ether. They may be used either singly or as a mixture of two or more. The amount of the polyalkylene glycol or its ether is not critical, and varies depending upon the types and amounts of impurities in the crude phenolic compound to be fed, and the quality (purity) of the desired phenolic compound. Generally, it is about 0.1 to about 10 parts by weight, preferably about 0.5 to about 5 parts by weight, per part by weight of the crude phenolic compound to be fed into the extractive distillation column.

The extractive distillation of the crude phenolic compound can be performed by a method known per se (for example, see Japanesse Patent Publication No. 5713/61). For example, in a distilling operation in an extractive distillation column, the operating conditions are selected depending upon the type of the polyalkylene glycol or its ether as an extraction solvent, etc. Generally, the extractive distillation is carried out at atmospheric pressure or under a reduced pressure of up to about 10 mmHg (absolute).

Desirably, the bottom temperature of the distillation column is set at a point at which decomposition and degeneration of the polyalkylene glycol or its ether do not take place, for example at a temperature of not more than 200° C. when diethylene glycol is used.

In the extractive distillation, it is recommended to feed the polyalkylene glycol or its ether to a tray above a tray to which the crude phenolic compound is fed, in the distillation column.

It is important that in the improved process of this invention, the extractive distillation is carried out under such conditions that the phenolic compound comes out from the top of the column in an amount of 0.3 to 30% by weight, preferably 0.5 to 25% by weight, more preferably 1 to 20% by weight, based on the total weight of the phenolic compound in the crude phenolic compound.

As a result of the extractive distillation operation under these specified conditions, detrimental impurities present in the crude phenolic compound are removed together with the phenolic compound as an overhead fraction. On the other hand, a fraction composed of the phenolic compound and the polyalkylene glycol or its ether and being free from impurities, particularly coloring impurities, can be obtained as a bottom fraction.

A method for operation which leads to the distillation of a specified amount of a phenolic compound in the crude phenolic compound fed as an overhead fraction in the above extractive distillation is obvious to those skilled in the art.

The extractive distillation step in the process of this invention is operated such that 0.3 to 30% by weight of the phenolic compound in the crude phenolic compound fed to the extractive distillation column is distilled out from the top of the column. In addition, the extractive distilling operation should preferably be controlled such that the concentration of the phenolic compound in the overhead fraction is generally at least 10% by weight, preferably at least 20% by weight.

The bottom fraction of the extractive distillation column operated under the above-specified conditions is substantially free from impurities, particularly coloring impurities, and consists substantially of the phenolic compound and the polyalkylene glycol or its ether. By an ordinary simple distilling operation, the bottom fraction can be separated into an overhead fraction composed of a purified phenolic compound of high quality and a bottom fraction composed of the fed polyalkylene glycol or its ether and a small amount of the phenolic compound. This bottom fraction can be recycled to the extractive distillation column.

Since the overhead fraction from the extractive distillation column containing the phenolic compound and impurities contains a considerable amount of the phenolic compound, it is subjected to steam distillation in order to recover it. A greater part of the phenolic compound is recovered as a distillation bottom of the steam distillation, and the recovered fraction rich in the phenolic compound is recycled to any step after the step of catalytical acid cleavage of the aralkyl hydroperoxide and before the extractive distillation step. The use of steam distillation for recovery of the phenolic compound to be recycled is most rational in order to recover the phenolic compound, and this is another important feature of the improved process of this invention.

The steam distillation step serves to recover the phenolic compound effectively, and to ensure production of a phenolic compound of high quality by discharging a considerable portion of the impurities in the crude phenolic compound fed to the extractive distillation step out of the system of phenol production and thereby preventing accumulation of the impurities in the system. Preferably, therefore, the steam distillation step is operated such that the components of the overhead fraction of the extractive distillation other than the phenolic compound (namely, at least about 20%, preferably at least about 50% by weight, most preferably at least about 70% by weight, of the impurities) are collected as an overhead fraction, and at least about 50% by weight, preferably at least about 70% by weight, more preferably at least about 90% by weight, of the phenolic compound in the extractive distillation fraction is collected as a bottom fraction.

It is recommended that the distilling operation in the steam distillation column be performed at atmospheric pressure or under a reduced pressure of up to about 100 mmHg (absolute) when the phenolic compound in the fraction to be treated is phenol or cresol, although this operating pressure may vary depending upon the type of the phenolic compound.

The amount of water used in steam distillation is not critical, but the suitable amount of water is generally about 0.05 to about 2.0 parts by weight, preferably about 0.1 to about 2.0 parts by weight, per part by weight of the overhead fraction from the extractive distillation column.

The overhead fraction of steam distillation is subjected to oil-water separation in accordance with a customary method, and an oil layer almost free from the phenolic compound is removed out of the system, and the aqueous layer is recycled to the steam distillation column. It is desirable that the amount of the aqueous phase to be recycled should be generally about 0.5 to about 3.0 parts by weight, per part by weight of the overhead fraction of the extraction distillation column.

The bottom fraction of the steam distillation column consists predominantly of the phenolic compound and water and contains small amounts of impurities. This fraction is recycled to any step after the step of catalytic acid cleavage of the aralkyl hydroperoxide and before the extractive distillation step. When there is a neutralization step between these steps, the fraction is preferably recycled to this step. But the step is not limited thereto, and when there is a fractional distillation step for removing by-products or impurities having lower and/or higher boiling points than the resulting phenolic compound, this fraction can of course be recycled to at least one distillation column in the fractional distillation step.

The amount of the bottom fraction of the steam distillation column to be recycled is not critical, and can be varied over a wide range depending upon the operating conditions, etc., in the extractive distillation step and/or the steam distillation step. Generally, all of the bottom fraction is recycled, and its amount corresponds to about 1 to about 15 parts by weight, calculated as the phenolic compound, per 100 parts by weight of the phenolic compound contained in the acid cleavage product.

Various methods may be used for recovering the phenolic compound from the overhead fraction of the extractive distillation column. However, a method involving using an alkali such as sodium hydroxide, for example, is not industrially feasible because the amount of the alkali is exceedingly large. With an ordinary fractional distillation operation, it is difficult to separate the phenolic compounds from those impurities which may degrade the quality of the phenolic compound, and when the recovered phenolic compound is recyclically used, the impurities gradually build up to make it impossible to obtain high quality phenolic compound in good yields. Another defect is that as a result of circulation of the accumulated impurities within the system, a loss of heat energy becomes considerably large. By employing the steam distilling method in accordance with the process of this invention, the recovered phenolic compound from which the impurities have been effectively separated can be used effectively as a recycle charge.

According to the improved process for producing a phenolic compound in this invention, in the extractive distillation of the crude phenolic compound with the polyalkylene glycol or its ether, by-products or impurities are removed as an overhead fraction of the extractive distillation column together with a relatively small amount of the phenolic compound. As a result, a relatively large amount of the purified phenolic compound separated from the bottom fraction of the extractive distillation column can be obtained as a product of high quality. Moreover, according to the process of this invention, the overhead fraction of the extractive distillation column is further submitted to steam distillation, and the phenol compound-containing fraction recovered is recycled to the crude phenolic compound prior to feeding to the extractive distillation column. Accordingly, the ratio of recovery of the phenol compound as a whole does not decrease. From the viewpoint of industrial operation, too, the process of this invention is a very rational and economical treating process because only the fractional distillation of the overhead fraction of the extractive distillation column and the step of recovering the phenolic compound-containing fraction by steam distillation of the overhead fraction are incorporated as additional steps. The process of this invention has the further advantage that the extracting solvent does not undergo degradation even when the process is industrially operated continuously for more than 1 year.

Thus, the process of this invention is essentially characterized by the fact that the step of extractive distillation in an extractive distillation column under specified conditions is combined with the step of steam distillation for recovering the phenol compound-rich fraction from the overhead fraction of the extractive distillation column. The combination of these steps makes it possible to obtain the phenolic compound of high quality in good yields. Furthermore, any desired process can be selected, without any particular restriction, for the production of a crude phenolic compound. The industrial advantage of the process of this invention is therefore significantly great.

The process of this invention is illustrated further by the following Examples with reference to the FIGURE which is a flow sheet. Unless otherwise specified, all parts and percentages in these Examples are by weight.

EXAMPLE 1

Cumene (purity 99.8%; containing 0.1% of ethylbenzene and 0.1% of cymene and butylbenzene combined) was oxidized with air at about 100° C., and the unreacted cumene was removed by distillation. The reaction product containing about 80% by weight of cumene hydroperoxide was cleaved at about 80° C. in the presence of about 0.2%, based on the weight of the reaction product, of sulfuric acid to decompose cumene hydroperoxide completely into phenol and acetone.

The resulting catalytic acid cleavage reaction consisted of about 36% of phenol, about 45% of acetone, about 14% of low-boiling hydrocarbons (having a boiling point of not more than 170° C.) such as cumene and alpha-methylstyrene and the balance consisting of mesityl oxide, hydroxyacetone, unidentified high-boiling hydrocarbons, acetophenone, and cumylphenol and sulfuric acid.

The acid cleavage product was introduced into a phenol purifying line shown in FIG. 1. Specifically, 288.66 parts of the acid cleavage product was fed into a neutralization tank 3 through a line 1, and 32.23 parts of an aqueous solution of sodium hydroxide was also fed into it through a line 2. From the neutralization tank 3, 6.04 parts of an aqueous solution of sodium sulfate was withdrawn through a line 4. In the meantime, 317.64 parts of the washed neutralization product of the acid cleavage product was sent to a first distillation column 6 through a line 5, and fractionally distilled under atmospheric pressure in the first distillation column 6. Through a line 7, a low-boiling fraction was taken out in a total amount of 201.51 parts. The low-boiling fraction consisted of about 64% of acetone, about 19% of low-boiling hydrocarbons such as cumene and alpha-methylstyrene, about 16% of water and the balance consisting of mesityl oxide and hydroxyacetone. The distillation bottom fraction in the first distillation column 6 was conducted to a second distillation column 9 through a line 8, and was fractionally distilled there to separate a high-boiling fraction at an overhead pressure of 300 mmHg. 12.03 Parts of a bottom fraction consisting of acetophenone and cumylphenols as main components (total about 50%) and small amounts of phenol and other compounds was withdrawn through a line 10.

The fraction distilled out from the top of the second distillation column 9 was crude phenol in an amount of 104.09 parts which consisted of 101.64 parts of phenol, about 1.91 parts of low-boiling hydrocarbons such as cumene and alpha-methylstyrene, about 0.25 part of high-boiling hydrocarbons such as benzofuran and phenylhexene and about 0.17 part of ketones such as mesityl oxide and hydroxyacetone. The crude phenol was sent to an extractive distillation column 12 through a line 11, and extractively distilled using as a solvent 233.32 parts of diethylene glycol containing about 23 parts of phenol which was fed into the top portion of the distillation column 12 through a line 13. The extractive distillation was operated at a column top pressure of about 100 mmHg (absolute) and a column top temperature of 117° C. and at a column bottom temperature of 185° C.

From the top of an extractive distillation column, 4.10 parts of an overhead fraction was obtained which consisted of 47.9% of low-boiling hydrocarbons such as cumene and alpha-methylstyrene, 6.9% of high-boiling hydrocarbons such as benzofuran and phenylhexane, 5.1% of ketones such as hydroxyacetone and mesityl oxide and 40.1% (corresponding to 1.64 parts) of phenol. The bottom fraction of the extractive distillation column was 333.32 parts of a mixture of phenol and diethylene glycol. The mixture was sent to a fractional distillation column 15 through a line 14, and distilled at a column top pressure of 100 mmHg (absolute) and a column top temperature of 122° C.

As a result of the distillation operation in the fractional distillation column, diethylene glycol as a high-boiling fraction was withdrawn through a line 13 in an amount of 233.32 parts (containing about 23 parts of phenol), and was recycled to the extractive distillation column 12 as an extractive distillation solvent. Phenol as a lower boiling fraction was recovered through a line 16 as a product. The amount of the product phenol was 100 parts (ratio of recovery 96.2%), and its sulfonation coloration value, defined below, was 94.

The sulfonation coloration value was determined as follows:

20 ml of a phenol sample was heated over a warm bath at 45° C. for 10 minutes, and then quickly mixed with 20 ml of conc. sulfuric acid. The mixture was allowed to stand at room temperature for 1 minute, and further in water for 5 minutes. The sample was transferred to a 20 mm cell, and its light transmittance at 532 m$\mu$ was measured by a photoelectric colorimeter, and expressed in %. The larger the sulfonation coloration value is, the better is the quality of the phenol.

The low-boiling fraction obtained at the extractive distillation column contained 1.64 parts of phenol, and therefore, phenol was distilled out at a rate of 1.61 parts by weight (1.64/101.64×100) per 100 parts by weight of phenol contained in the crude phenol. This fraction was conducted to a steam distillation column 18 through a line 17, and subjected to steam distillation at a column top pressure of 300 mmHg (absolute), a column top temperature of 76° C. and a column bottom temperature of 82° C. In performing the steam distillation, 1.08 parts of water was added through a line 19, and 8.66 parts of the water layer from an overhead distillate-separating tank 20 was recycled through a line 21. The oil layer (2.39 parts) contained about 5.4% of phenol in addition to impurities as major components, and was withdrawn from the separating tank through a line 22. On the other hand, the bottom fraction of the steam distillation column consisted of 1.51 parts of phenol, 1.08 parts of water and 0.20 part of impurities, and this phenol-containing fraction is recycled to the neutralization tank 3 through a line 23.

When the above process was continuously operated for one year, the quality of phenol could be retained without reducing the ratio of recovery of phenol, and no degradation of diethylene glycol was noted.

COMPARATIVE EXAMPLE 1

Extractive distillation using diethylene glycol and fractional distillation of phenol from the extractive distillation solvent were performed in the same way as in Example 1. Different features from Example 1 were as follows:

The amount of an aqueous solution of sodium hydroxide used for neutralization was 33.36 parts; the amount of the washed neutralization product of the acid cleavage product was 315.98 parts; the amount of a low-boiling fraction in the first distillation column was 201.43 parts; and the amount of crude phenol was 102.52 parts (100.13 parts as phenol). These amounts were substantially the same as those in Example 1.

The extractive distillation operation was performed at a column top pressure of 100 mmHg (absolute), a column top temperature of 110° C. and a column bottom temperature of 185° C. As a result, 252 parts of an overhead fraction was obtained, which consisted of about 78% of low-boiling hydrocarbons such as cumene and alpha-methylstyrene, about 10% of high-boiling hydrocarbons such as benzofuran and phenylhexane, about 7% of ketones such as hydroxyacetone and mesityl oxide, and about 5% of phenol (corresponding to 0.13 part; thus phenol was distilled at a rate of 0.13 part by weight per 100 parts by weight of the crude phenol, as calculated from 0.13/100.13×100).

The bottom fraction of the extractive distillation column was fractionally distilled. 100 Parts of product phenol separated from diethylene glycol was obtained. It had a sulfonation coloration value of only 58%.

EXAMPLE 2

Cumene (purity 99.8%; containing 0.1% of ethylbenzene and 0.1% of cymene and butylbenzene combined) was oxidized with air at about 100° C., and the unreacted cumene was removed by distillation. The resulting reaction product containing about 80% by weight of cumene hydroperoxide was cleaved at about 80° c. in the presence of about 0.2%, based on the weight of the reaction product, of sulfuric acid to decompose cumene hydroperoxide completely into phenol and acetone.

The resulting catalytic acid cleavage reaction consisted of about 36% of phenol, about 45% of acetone, about 14% of low-boiling hydrocarbons (having a boiling point of not more than 170° C.) such as cumene and alpha-methylstyrene and the balance consisting of mesityl oxide, hydroxyacetone, unidentified high-boiling hydrocarbons, acetophenone, and cumylphenol and sulfuric acid.

The acid cleavage product was introduced into a phenol purifying line shown in FIG. 1. Specifically, 288.57 parts of the acid cleavage product was fed into a neutralization tank 3 through a line 1, and 31.18 parts of an aqueous solution of sodium hydroxide was also fed into it through a line 2. From the neutralization tank 3, 6.04 parts of an aqueous solution of sodium sulfate was withdrawn through a line 4. In the meantime, 325.65 parts of the washed neutralization product of the acid cleavage product was sent to a first distillation column 6 through a line 5, and fractionally distilled under atmospheric pressure in the first distillation column 6. Through a line 7, a low-boiling fraction was taken out in a total amount of 202.84 parts. The low-boiling fraction consisted of about 64% of acetone, about 20% of low-boiling hydrocarbons such as cumene and alpha-methylstyrene, about 16% of water and the balance consisting of mesityl oxide and hydroxyacetone. The distillation bottom fraction in the first distillation column 6 was conducted to a second distillation column 9 through a line 8, and was fractionally distilled there to separate a high-boiling fraction at an overhead pressure of 300 mmHg. A bottom fraction (11.85 parts) consisting of acetophenone and cumylphenols as main components (total about 50%) and small amounts of phenol and other compounds was withdrawn through a line 10.

The fraction distilled out from the top of the second distillation column 9 was crude phenol in an amount of 110.96 parts which consisted of 109.57 parts of phenol, about 0.59 part of low-boiling hydrocarbons such as cumene and alpha-methylstyrene, about 0.30 part of high-boiling hydrocarbons such as benzofuran and phenylhexane and about 0.50 part of ketones such as mesityl oxide and hydroxyacetone. The crude phenol was sent to an extractive distillation column 12 through a line 11, and extractively distilled using as a solvent 262 parts of diethylene glycol containing about 43 parts of phenol which was fed into the top portion of the distillation column 12 through a line 13. The extractive distillation was operated at a column top pressure of about 100 mmHg (absolute) and a column top temperature of 117° C. and at a column bottom temperature of 185° C.

From the top of the extractive distillation column, 10.96 parts of an overhead fraction was obtained which consisted of 5.42% of low-boiling hydrocarbons such as cumene and alpha-methylstyrene, 2.7% of high-boiling hydrocarbons such as benzofuran and phenylhexene, 4.56% of ketones such as hydroxyacetone and mesityl oxide and 87.32% (corresponding to 9.57 parts) of phenol. The bottom fraction of the extractive distillation column was 365 parts of a mixture of phenol and diethylene glycol. The mixture was sent to a fractional distillation column 15 through a line 14, and distilled at a column top pressure of 100 mmHg (absolute) and a column top temperature of 122° C.

As a result of the distillation operation in the fractional distillation column, diethylene glycol as a high-boiling fraction was withdrawn through a line 13 in an amount of 265 parts (containing about 23 parts of phenol), and was recycled to the extractive distillation column 12 as an extractive distillation solvent. Phenol as a lower boiling fraction was recovered through a line 16 as a product. The amount of the product phenol was 100 parts (ratio of recovery 97%), and its sulfonation coloration value, defined below, was 95%.

The sulfonation coloration value was determined as follows:

20 ml of phenol sample was heated over a warm bath at 45° C. for 10 minutes, and then quickly mixed with 20 ml of conc. sulfuric acid. The mixture was allowed to stand at room temperature for 1 minute, and further in water for 5 minutes. The sample was transferred to a 20 mm cell, and its light transmittance at 532 mμ was measured by a photoselective colorimeter, and expressed in %. The larger the sulfonation coloration value is, the better is the quality of the phenol.

The low-boiling fraction obtained at the extractive distillation column contained 1.64 parts of phenol, and therefore, phenol was distilled out at a rate of 8.73 parts by weight (9.57/109.57×100) per 100 parts by weight of phenol contained in the crude phenol. This fraction was conducted to a steam distillation column 18 through a line 17, and subjected to steam distillation at a column top pressure of 300 mmHg (absolute), a column top temperature of 76° C. and a column bottom temperature of 82° C. In performing the steam distillation, 2.10 parts of water was added through a line 19, and 14.7 parts of the water layer from an overhead distillate-separating tank 20 was fed through a line 21. The oil layer fraction (1.32 parts) contained about 17% of phenol in addition to impurities as major components, and was withdrawn from the separating tank through a line 22. On the other hand, the bottom fraction of the steam distillation column consisted of 9.35 parts of phenol, 2.1 parts of water and 0.29 part of impurities, and this phenol-containing fraction is recycled to the neutralization tank 3 through a line 23.

When the above process was continuously operated for one year, the quality of phenol could be retained without reducing the ratio of recovery of phenol, and no degradation of diethylene glycol was noted.

What we claim is:

1. In a process for producing a phenolic compound which comprises
    catalytically cleaving an aralkyl hydroperoxide with an acid to form a phenolic compound,
    removing the acid and by-products or impurities having lower and/or higher boiling points than the resulting phenolic compound to recover a crude phenolic compound,
    feeding the recovered crude phenolic compound to an extractive distillation column and extractively distilling it in the presence of a polyalkylene glycol or its ether having a higher boiling point than the phenolic compound to separate the phenolic compound and the polyalkylene glycol or its ether as a bottom fraction, and
    separating the bottom fraction into the phenolic compound and the polyalkylene glycol or its ether; the improvement wherein
    (a) carrying out the extractive distillation under such conditions that the phenolic compound comes out from the top of the column in an amount of 0.3 to 30% by weight based on the total weight of the phenolic compound in the crude phenolic compound fed to the extractive distillation column, and
    (b) subjecting the phenol compound-containing overhead fraction from the extractive distillation column to steam distillation and the resulting bottom fraction containing the phenolic compound is recycled to any step after said step of catalytic acid cleavage and before said step of extractive distillation.

2. The process of claim 1 wherein the extractive distillation is carried out under such conditions that the phenolic compound comes out from the top of the column in an amount of 0.5 to 25% by weight based on the total weight of the phenolic compound in the crude phenolic compound fed to the extractive distillation column.

3. The process of claim 1 wherein the overhead fraction of the extractive distillation column contains at least 10% by weight of the phenolic compound.

4. The process of claim 1 wherein the polyalkylene glycol or its ether has a boiling point at least 20° C. higher than the phenolic compound.

5. The process of claim 1 wherein the polyalkylene glycol or its ether is diethylene glycol, triethylene glycol, dipropylene glycol, diethylene glycol methyl ether, diethylene glycol propyl ether, diethylene glycol butyl ether, or a mixture of two or more of these compounds.

6. The process of claim 1 wherein the extractive distillation is carried out in the presence of about 0.1 to about 10 parts by weight of the polyalkylene glycol or its ether per part by weight of the crude phenolic compound.

7. The process of claim 1 wherein the steam distillation is carried out by feeding about 0.05 to about 2.0 parts by weight, per part by weight of the phenolic compound-containing overhead fraction, of water.

8. The process of claim 1 wherein the phenolic compound contained in the bottom fraction of the steam distillation contains at least 50% by weight of the phenolic compound contained in the overhead fraction of the extractive distillation.

9. The process of claim 1 wherein the overhead fraction of the steam distillation contains at least about 20% by weight of the impurities contained in the phenolic compound-containing overhead fraction of the extractive distillation.

10. The process of claim 1 wherein the bottom fraction of the steam distillation is recycled to the step of neutralizing the acid cleavage product.

11. The process of claim 1 wherein the aralkyl hydroperoxide is cumene hydroperoxide, and the phenolic compound is phenol.

* * * * *

UNITED STATES PATENT AND TRADEMARK OFFICE
CERTIFICATE OF CORRECTION

PATENT NO. : 4,351,967
DATED : September 28, 1982
INVENTOR(S) : Tadahiko Nishimura, Masatoshi Yamamoto, Hiroshi Osuo and Akio Kanazawa It is certified that error appears in the above—identified patent and that said Letters Patent is hereby corrected as shown below:

ON THE TITLE PAGE,
Inventors: Tadahiko Nishimura, Iwakuni;
Masatoshi Yamamoto, Ichihara
Hiroshi Osuo, Ichihara
Akio Kanazawa, Ichihara Signed and Sealed this Twenty-third Day of November 1982

[SEAL]

Attest:

GERALD J. MOSSINGHOFF

Attesting Officer

Commissioner of Patents and Trademarks